United States Patent [19]

Knudson, Jr.

[11] Patent Number: 4,849,006

[45] Date of Patent: Jul. 18, 1989

[54] CONTROLLED RELEASE COMPOSITION AND METHOD

[75] Inventor: Milburn I. Knudson, Jr., Gonzales, Tex.

[73] Assignee: E.C.C. America Inc., Atlanta, Ga.

[21] Appl. No.: 83,470

[22] Filed: Aug. 7, 1987

[51] Int. Cl.[4] .............. A01N 25/00
[52] U.S. Cl. .............. 71/64.11; 71/904
[58] Field of Search .............. 71/64.11, 904

[56] References Cited

U.S. PATENT DOCUMENTS

| | | | |
|---|---|---|---|
| 2,982,665 | 5/1961 | Wilcox | 71/904 |
| 3,050,385 | 8/1962 | Parker . | |
| 3,062,637 | 11/1962 | Marples | 71/2.4 |
| 3,192,031 | 6/1965 | Zaayenga | 71/28 |
| 3,502,458 | 3/1970 | Schenk . | |
| 4,040,974 | 8/1977 | Wright et al. | 252/316 |
| 4,067,961 | 1/1978 | Laughlin . | |
| 4,082,533 | 4/1978 | Wittenbrook et al. . | |
| 4,105,578 | 8/1978 | Finlayson et al. . | |
| 4,123,248 | 10/1978 | Drake | 76/64.1 X |
| 4,145,408 | 3/1979 | Laughlin . | |
| 4,182,620 | 1/1980 | Denninger et al. . | |
| 4,219,349 | 8/1980 | Bardsley . | |
| 4,280,833 | 7/1981 | Beestman et al. . | |
| 4,282,207 | 8/1981 | Young et al. . | |
| 4,283,387 | 8/1981 | Young et al. . | |
| 4,412,018 | 10/1983 | Finlayson et al. . | |
| 4,469,639 | 9/1984 | Thompson, III et al. . | |
| 4,470,912 | 9/1984 | Beall . | |
| 4,473,477 | 9/1984 | Beall . | |
| 4,517,094 | 5/1985 | Beall . | |
| 4,549,966 | 10/1985 | Beall . | |
| 4,569,923 | 2/1986 | Knudson, Jr. et al. . | |
| 4,621,070 | 11/1986 | Pinnavaia et al. | 502/63 |
| 4,623,398 | 11/1986 | Goodman et al. . | |
| 4,683,259 | 7/1987 | Goodman . | |

FOREIGN PATENT DOCUMENTS

| | | |
|---|---|---|
| 61-031377 | 2/1986 | Japan . |
| 0793964 | 1/1981 | U.S.S.R. . |
| 1161503 | 6/1985 | U.S.S.R. . |
| 2127004 | 4/1984 | United Kingdom . |
| 79000261 | 5/1979 | World Int. Prop. O. . |

OTHER PUBLICATIONS

*Dictionary of Ceramics*, A. Dodd, Philosophical Library, Inc. N.Y. (1964) pp. 135, 263.
Howley, G. *The Condensed Chemical Dictionary*, 10th Ed., Van Nostrand Co., N.Y. (1981) pp. 255-6, 1105-6.
Rock-Forming Minerals, vol. 4, Framework Silicates, W. A. Deer et al., pp. 351-352.
An Introduction to Clay Colloid Chemistry, 2nd Ed., H. van Olphen, pp. 64-65.
Clay Mineralogy, 2nd Ed., Ralph E. Grim, pp. 57-59.
Clay Mineralogy, Second Edition, Ralph E. Grim, Author, published by McGraw-Hill Book Co.

*Primary Examiner*—WIlliam R. Dixon, Jr.
*Assistant Examiner*—Andrew Griffis
*Attorney, Agent, or Firm*—Klauber & Jackson

[57] ABSTRACT

A controlled release composition is prepared by contacting an organoclay with a biologically active material in concentrated form to cause absorption of the active material on the organoclay. The resulting product releases the active agent slowly, over a period of time, when exposed to the open atmosphere, for instance on being distributed over cultivated fields.

7 Claims, 3 Drawing Sheets

CONTROLLED RELEASE COMPOSITION AND METHOD

FIELD OF THE INVENTION

This invention relates to a composition and method for the controlled release of biologically active agricultural agents such as fertilizers and more specifically pesticides. More specifically, the invention concerns the absorption, on a particular type of material, of certain organic agents such as herbicides and the like which would be released over a time span once the product is dispersed in the field.

BACKGROUND OF THE INVENTION

The basic principle in controlled release is the entrapment of an active ingredient by some method in such a way that slow escape of the ingredient to the environment is allowed, see Agis Kydonieus, *Controlled Release Technologies: Methods, Theory and Applications,* pages 2 and 4, CRC Press, Inc. 1980.

The use of time-release agents for agricultural purposes in cultivated field environments is known. In many instances the means used for controlling release of the active ingredient over a period of time has been chosen to reduce the exposure thereof to the environment so as to prevent its being quickly washed away by water or to prevent rapid evaporation. Consequently, the effort has frequently been to coat the active ingredient with one or more insoluble materials, thereby to slow down its movement into the environment.

Thus, for example, U.S. Pat. No. 4,082,533 discloses a product having a core of a urea fertilizer and two water-insoluble coatings, viz., cement and a thermoplastic polymer/wax blend. The patentee of U.S. Pat. No. 3,050,385 bonds the fertilizer to oil shale as an insolubilizing and support material. U.S. Pat. No. 3,502,458 uses a fertilizer, a dry fibrous organic material such as sawdust and a bonding agent such as a urea-formaldehyde resin or a Cumar V-3 resin. U.S. Pat. No. 3,192,031 discloses urea (fertilizer) particles precoated with a thin film of a diatomaceous earth (natural clays, e.g. bentonite, are briefly mentioned) and then coated with wax. U.S. Pat. No. 3,062,637 describes an agricultural granule for insecticide, herbicide and plant nutrient purposes, which comprises the active ingredient, a mineral carrier such as diatomaceous earth and as a binder a colloidal clay, viz., attapulgite or sepiolite.

On the other hand, water-immiscible herbicides and the like are used which are formed into aqueous dispersions with the aid of emulsifiers and then encapsulated, as disclosed in U.S. Pat. No. 4,280,833. Controlled release pesticides are also formulated with silanes as shown in U.S. Pat. Nos. 4,282,207 and 4,283,387.

In the medical/biochemical area, compositions are used in which the medically active components in solution are releasably enclosed within a container at least part of which is a microporous membrane. In this category fall U.S. Pat. Nos. 4,067,961 and 4,145,408.

A solid pesticide adapted to be progressively disintegrated by contact with a stream of water is described in U.S. Pat. No. 4,182,620. It comprises a pesticide, a solid non-hydrophilic filler such as talcum and a starch. Kaolin is included in some of the compositions.

U.S. Pat. No. 4,219,349 discloses a plant nutrient composition, for potted plants containing little mineral soil but instead containing growth media, and comprising various plant nutrients on a calcined clay which may be bentonite or attapulgite. As described, the compositions are prepared by mixing the calcined clay granules with a solution of the nutrients. The compositions are applied to the growth media in plant nourishing amounts. The patentee theorizes that when the plant nutrient compositions are incorporated into the growth media they will equilibrate with the solution bathing the roots and the media; the plant roots exchange protons and bicarbonates for the needed ions in solution which in turn exchange with the micronutrients on the clay granules to supply nutrients to complete the cycle.

Thus, the plant nutrient compositions function via an ion exchange process with plant roots in an aqueous medium.

In a series of U.S. patents to Gary W. Beall, assigned to Radecca, Inc., which are:

No. 4,470,912
No. 4,473,477
No. 4,517,094
No. 4,549,966 a method is described for absorbing organic contaminants on an organoclay from an aqueous composition or from solid or liquid wastes.

Organoclays are well known in the art, especially as gelling agents for paints and the like. In this invention, the term "organoclay" refers to various clay types, e.g. smectites, that have organo ammonium ions substituted for cations between the clay layers. The term "organo ammonium ion" refers to a substituted ammonium ion in which one or more hydrogen atoms are replaced by an organic group. The organoclays are modified clays which exhibit in organic liquids, some of those characteristics which untreated clays exhibit in water. For example, they will swell in many organic liquids and will form stable gels and colloidal dispersions. Organoclays are organophilic or oleophilic. An extensive discussion may be found in the above-mentioned patents to Beall.

According to the invention, organic bioactive agents such as fertilizers and pesticides, e.g. insecticides, herbicides, bactericides, growth regulators and fungicides, may be controllably released by a unique mechanism which is independent on the absorptive/desorptive characteristics of a particular material on which the agents are provided.

SUMMARY OF THE INVENTION

In accordance with the invention, a controlled release composition is provided which comprises an organoclay on which an organic biologically active material has been absorbed. The method of application involves exposing the organoclay to a high concentration of the active ingredient to cause it to be absorbed on the organoclay and then distributing the product in agricultural fields where it is needed. This function of organoclays is surprising since they have previously been used primarily as gelling agents; also they have been proposed in the Beall patents for absorbing organic contaminants but not for slow release or distribution of biologically active materials where needed, particularly for improving agriculture.

DETAILED DESCRIPTION

Figure 1:
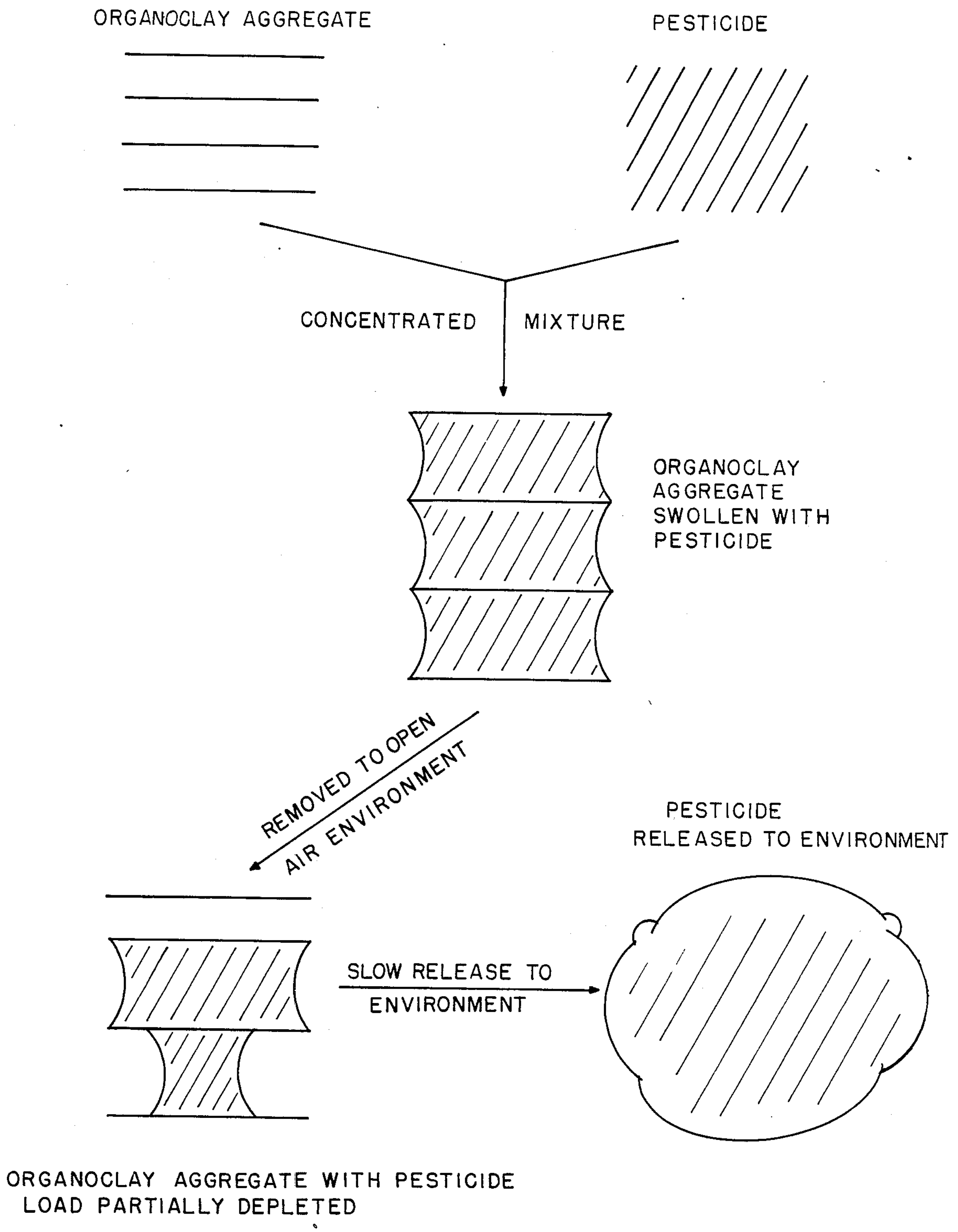
FIG. 1 is a flowsheet illustrating how organoclays can be used in controlled release applications.

The preferred clay substrates for use in this invention are the smectite type clays, particularly the smectite type clays which have a cation exchange capacity of at least 75 milliequivalents per 100 grams of clay. Useful clays for such purposes include the naturally occurring Wyoming variety of swelling bentonite and similar clays, and hectorite, which is a swelling magnesium-lithium silicate clay. The clays are preferably converted to the sodium form if they are not already in this form. This can be effected by a cation exchange reaction with a soluble sodium compound. These methods are well known in the art. Smectite-type clays prepared synthetically can also be utilized.

Generally, the quaternary ammonium salt reacted with the clay has organic groups attached to the quaternary nitrogen which may range from aliphatic hydrocarbon of from 1 to 24 carbons to aromatic organic molecules, such as benzyl groups that could have a host of groups substituted on the benzyl ring. The amount of alkyl ammonium salt substituted on the clay can vary between 0.5% to 50%.

In particular, the organoclay used in this invention may comprise one or more of the following ammonium cation modified montmorillonite clays:

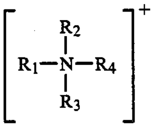 Montmorillonite - wherein $R_1$ is an alkyl group having at least 4 carbon atoms, preferably at least 10 carbon atoms and up to, for example, 24 carbon atoms, more preferably having a chain length of from 12 to 18 carbon atoms; $R_2$ is hydrogen, benzyl or an alkyl group of at least 4 carbon atoms, preferably at least 10 carbon atoms and up to, for example, 24 carbon atoms, more preferably a chain length of from 12 to 18 carbon atoms; and $R_3$ and $R_4$are each hydrogen or lower alkyl groups, viz., they contain carbon chains of from 1 to 4 atoms, and preferably are methyl groups. Hydroxyethoxy, hydroxypropoxy groups and their corresponding poly-oxy homologs are also especially useful in some applications.

Other organoclays utilizable in the invention include benzyl organoclays such as dimethyl benzyl (hydrogenated tallow) ammonium bentonite; methyl benzyl di(-hydrogenated tallow) ammonium bentonite; and more generally quaternary ammonium cation modified montmorillonite clays represented by the formula:

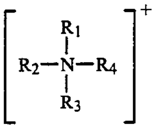 Montomorillonite - wherein $R_1$ is $CH_3$ or $C_6H_5CH_2$; $R_2$ is $C_6H_5CH_2$; and $R_3$ and $R_4$ are alkyl groups containing long chain alkyl radicals having 14 to 22 carbon atoms, and most preferably wherein 20% to 35% of said long chain alkyl radicals contain 16 carbon atoms and 60% to 75% of said long chain alkyl radicals contain 18 carbon atoms.

The montmorillonite clays which may be so modified are the principal constituents of bentonite rock. Modified montmorillonite clays of this type (i.e. organoclays) are commercially available from Southern Clay Products, Inc., Gonzales, Tex., under such trade designations as CLAYTONE 34 and 40, and are available from NL Industries, Inc. New York, N.Y., under such trade designations as BENTONE 27, 34, and 38. The preferred organoclays utilized in this invention, are the higher dialky dimethyl ammonium organoclays such as dimethyl di(hydrogenated tallow) ammonium bentonite; the benzyl ammonium organoclays, such as dimethyl benzyl (hydrogenated tallow) ammonium bentonite; and hydroxyethoxy ammonium organoclays such as methyl bis(2-hydroxyethoxy)octadecyl ammonium bentonite.

FIG. 1 illustrates how organoclays can be used in controlled release applications. The organoclay is first exposed to a high concentration of the active ingredient. The active ingredient is absorbed into the clay interlayers and held there by capillary and/or solvation forces until an equilibrium concentration is reached within the organoclay. This equilibrium concentration depends on the concentration of the active in contact with the organoclay. As the concentration of the active in contact with the clay decreases, so does the capacity of the clay for the active. Thus, when the clay which has been in contact with a high active concentration is removed to an environment which is low in active, the clay gives off its absorbed active until a new equilibrium is reached with the new environment (which may be air, water, etc.). Thus, if the organoclay is placed in pure liquid pesticide, it will absorb some quantity of the pesticide. If it is then removed to the open atmosphere, it will allow the absorbed pesticide to escape into the environment. However, the rate of release (or escape) will be much slower than if one simply left a drop of the same amount of pesticide out on a dish (assuming a volatile pesticide is used). Thus, the pesticide absorbed on organoclay gives a more prolonged effect than the pesticide by itself.

The method of contacting the organoclay with the organic biologically active material may be any of those described in U.S. Pat. No. 4,549,966, for example, by using flow through columns and batch methods, e.g., flowing the organic, which may be in a concentrated solution, through a packed column of organoclay; or by contacting stirred beds of organoclay with the treating composition; or by adding to the latter the organoclay as a finely divided powder and after a sufficient time separating it by known methods such as filtration, centrifugation, etc. It is also possible to mix the organic biologically active material with the quaternary ammonium compound prior to reacting the quaternary ammonium compound with the bentonite to form the organoclay.

Application of the product in fields may be done by any of the conventional methods, e.g., broadcasting from the air, spraying, etc.

The invention is demonstrated in the following examples which are to be considered illustrative but not limitative.

EXAMPLE 1

Figure 2:
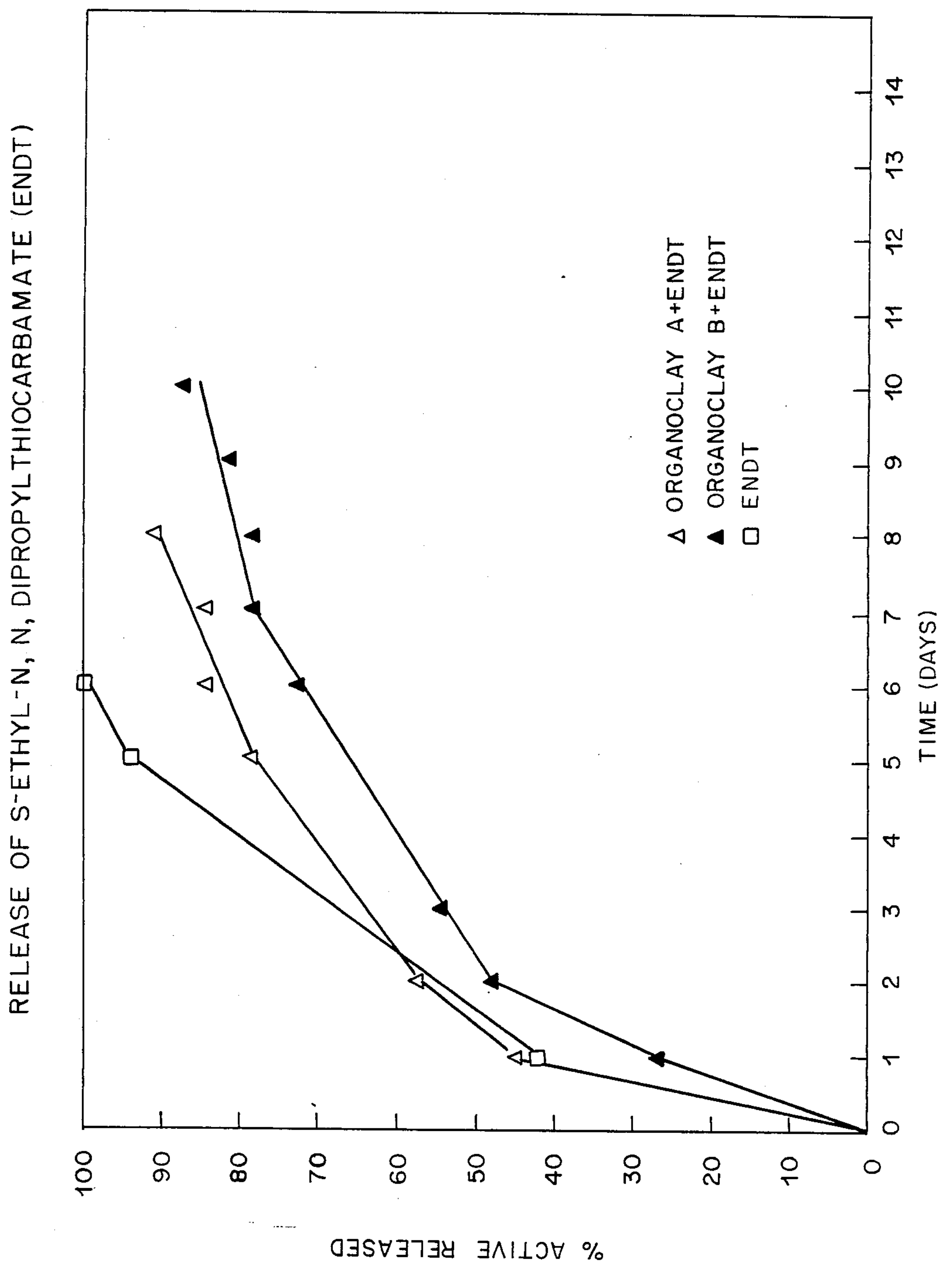
FIG. 2 is a graph showing the release of a biologically active material from two different organoclays on which it has been absorbed, in which the percent of the active material which has been released from the organoclay exposed to a controlled flow of nitrogen is plotted against time, in days.

Two samples of S-Ethyl-N,N,dipropylthiocarbamate (ENDT) were mixed respectively with two different, dry powdered organoclays to form controlled release compositions and allowed to sit overnight. The ratio of organoclay to ENDT was 2:1 in each case. The weight loss of three separate containers (pure ENDT and the two ENDT/organoclay mixtures) was measured over a period of 10 days. Each container was kept in a stream of nitrogen flowing at 6000 cc/min. The results are shown in FIG. 2. The organoclays clearly slow the release of ENDT.

The organoclays in this example were both made from the same bentonite. However, organoclay A contained 100 meq/100 g clay of the diemthyldi(hydrogenated tallow) ammonium cation whereas organoclay B contained 92 meq/100 g clay of the trimethyldodecyl ammonium chloride cation. Clearly, the type of organic ammonium compound used to make the organoclay can have a significant effect on the rate of release of some absorbed organic materials.

ENDT is used commercially as a herbicide, especially in the production of corn.

EXAMPLE 2

S-Ethyldiisobutylthiocarbamate (EDBT) sold under the tradename "Genate" was mixed with organoclay A in the same manner as in Example 1. The EDBT/organoclay composition was then placed in a nitrogen air stream flowing at 6,000 cc/min. The amount of EDBT in the nitrogen stream downflow from the EDBT/organoclay composition was measured after one hour and then on selected days thereafter for 25 days. Gas chromatography was used to measure the EDBT.

Figure 3:
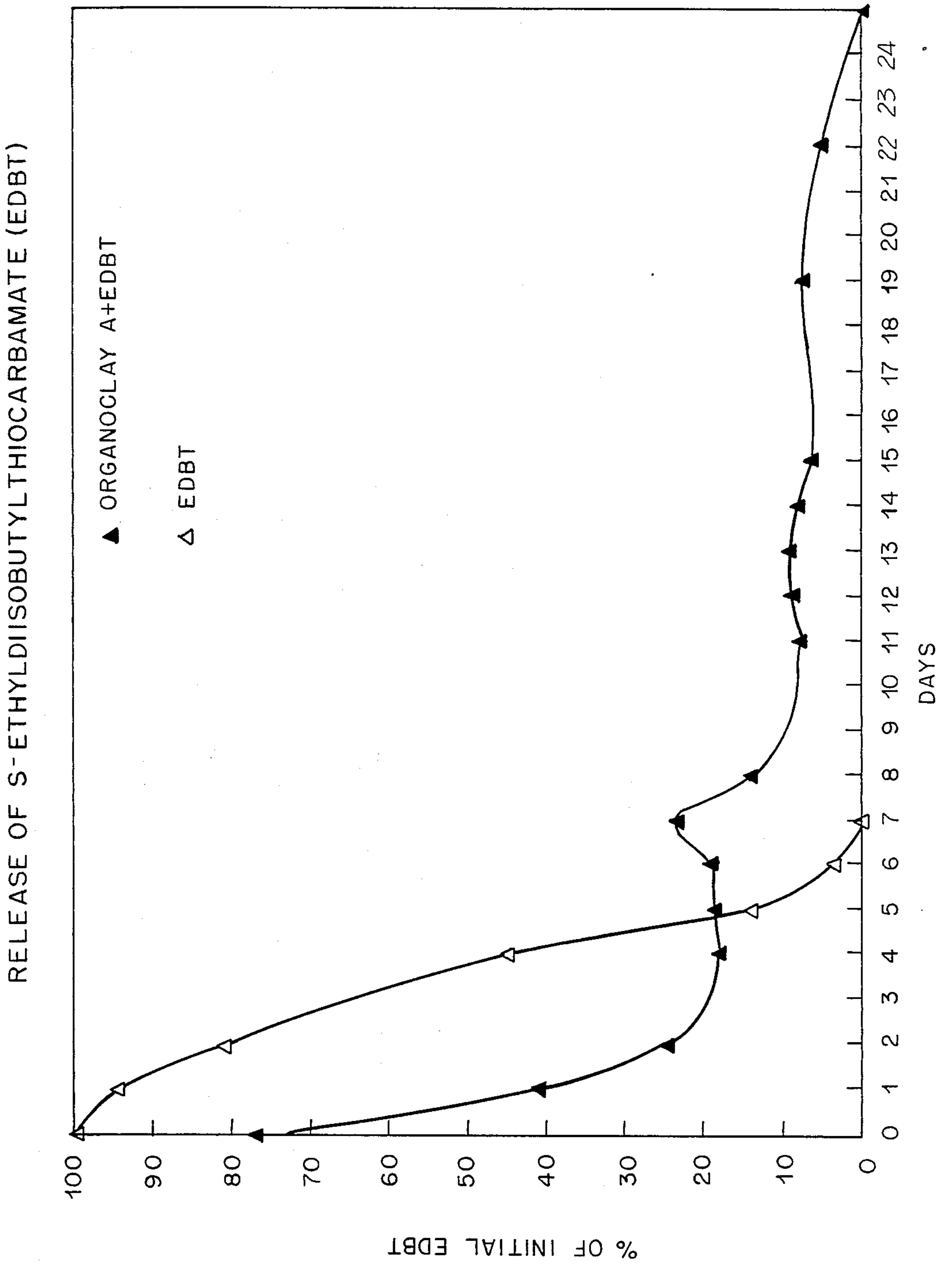
FIG. 3 shows the amount of a biologically active material present in a stream of nitrogen continually passed over the active material alone as well as the amount present in a separate flow passed over the active material which has been absorbed onto an organoclay.

FIG. 3 shows that the release of EDBT is dramatically prolonged by the organoclay relative to evaporation of the pure liquid EDBT.

Like ENDT, EDBT is an effective herbicide used in controlling weeds in corn production.

It can be seen that the use of organoclays in controlled release pesticides is a novel and useful approach. The behavior of the product is largely dependent on the intrinsic absorptive/desorptive properties of the organoclay for organic substances and thus is not suggested by other types of carriers/supports. It is not necessary to mix the pesticide with highly insoluble materials of the nature of cement, oil shale, and the like; or on the other hand to make a dispersion thereof; or to enclose the pesticide within a membrance sac. In fact, it is not mandatory to formulate the two essential ingredients with other ingredients, although such is not precluded in the subject invention. The subject invention is operable in a simplified mode; works by a distinctive, novel mechanism; permits the controlled passage into the environment of an active substance because of the initial dilution of the biologically active ingredient with the admixed innocuous solid clay and the slow release feature, thus avoiding high concentrations of the active agent, and is unique in many of its aspects.

What is claimed is:

1. A controlled release composition for the distribution of an organic pesticide in agriculturally cultivated fields which comprises an organoclay on which said pesticide in liquid form has been absorbed, said organoclay being a smectite clay in which organo ammonium ions have been substituted for cations between the clay layers and the substituted ammonium ion has one or more hydrogen atoms replaced by an organic group, whereby the oleophilic organo ammonium ion functions in absorbing the organic pesticide.

2. The composition as set forth in claim 1 in which the organoclay is a $C_{12}$ to $C_{18}$-dialkyl dimethyl ammonium organoclay.

3. The composition as set forth in claim 1 in which the organoclay is a benzyl ammonium organoclay.

4. The composition of claim 1 in which the organoclay is a hydroxyalkoxy ammonium organoclay.

5. A composition as set forth in claim 1 in which the organoclay comprises one or more of the following ammonium cation modified montmorilonite clays:

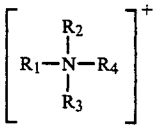

Montmorillonite - wherein $R_1$ is an alkyl group of 4–24 carbon atoms; $R_2$ is hydrogen, benzyl or an alkyl group of 4–24 carbon atoms; and $R_3$ and $R_4$ are each hydrogen or alkyl of 1 to 4 carbon atoms.

6. A method of preparing a controlled release composition which comprises contacting an organoclay with a liquid organic pesticide in concentrated form to cause absorption of the pesticide by the organoclay said organoclay being a smectite clay in which organo ammonium ions have been substituted for cations between the clay layers and the substituted ammonium ion has one or more hydrogen atoms replaced by an organic group, whereby the oleophilic organo ammonium ion functions in absorbing the organic pesticide.

7. A method of preparing a controlled release composition which comprises mixing a liquid organic pesticide with an organic ammonium salt in which one or more hydrogen atoms have been replaced by an organic group, and converting the salt to an organoclay by addition of a smectite clay, whereby the oleophilic organo ammonium ion functions in absorbing the organic pesticide.

* * * * *